United States Patent
Walton et al.

(10) Patent No.: US 7,806,860 B2
(45) Date of Patent: Oct. 5, 2010

(54) SAFETY SYRINGE WITH PLUNGER LOCKING MEANS

(75) Inventors: Graeme Francis Walton, Newcastle (AU); Allan Walsh, Medowie (AU)

(73) Assignee: Global Medisafe Holdings Limited (AU)

( * ) Notice: Subject to any disclaimer, the term of this patent is extended or adjusted under 35 U.S.C. 154(b) by 0 days.

(21) Appl. No.: 12/093,775

(22) PCT Filed: Mar. 10, 2006

(86) PCT No.: PCT/AU2006/000320

§ 371 (c)(1),
(2), (4) Date: May 15, 2008

(87) PCT Pub. No.: WO2007/056792

PCT Pub. Date: May 24, 2007

(65) Prior Publication Data

US 2008/0281266 A1 Nov. 13, 2008

(30) Foreign Application Priority Data

Nov. 15, 2005 (AU) .............................. 2005906318
Jan. 23, 2006 (AU) .............................. 2006900314

(51) Int. Cl.
*A61M 5/00* (2006.01)
(52) U.S. Cl. ...................................... 604/110
(58) Field of Classification Search ................. 604/110
See application file for complete search history.

(56) References Cited

U.S. PATENT DOCUMENTS

| 4,507,117 A | 3/1985 | Vining et al. |
| 4,650,468 A | 3/1987 | Jennings, Jr. |
| 4,675,005 A | 6/1987 | DeLuccia |
| 4,747,830 A | 5/1988 | Gloyer et al. |
| 4,790,822 A | 12/1988 | Haining |
| 4,946,446 A | 8/1990 | Vadher |
| 4,969,877 A | 11/1990 | Kornberg |
| 4,986,813 A | 1/1991 | Blake, III et al. |
| 5,066,281 A | 11/1991 | Stevenson-Michener |
| 5,114,404 A | 5/1992 | Paxton et al. |
| 5,163,907 A | 11/1992 | Szuszkiewicz |
| 5,188,601 A | 2/1993 | King |

(Continued)

FOREIGN PATENT DOCUMENTS

AU 2004/201893 A1 12/2004

(Continued)

OTHER PUBLICATIONS

International Search Report, PCT/AU2006/000320.

*Primary Examiner*—Nicholas D Lucchesi
*Assistant Examiner*—Rebecca E Eisenberg
(74) *Attorney, Agent, or Firm*—Brooks Kushman P.C.

(57) ABSTRACT

A safety syringe is disclosed. The safety syringe has a retractable needle facility incorporated therein, the syringe comprising a barrel and plunger and needle assembly. The needle is caused to retract into the barrel of the syringe upon completion of injection once it has been used, by means of engagement between the needle assembly and the end of the plunger. Locking means preferably in the form of a locking bush is provided in the body of the syringe to engage the plunger once it is retracted after use, so that the syringe is rendered incapable of being used further.

22 Claims, 6 Drawing Sheets

U.S. PATENT DOCUMENTS

| | | | |
|---|---|---|---|
| 5,209,732 A * | 5/1993 | Lampropoulos et al. | 604/99.01 |
| 5,222,944 A | 6/1993 | Harris | |
| 5,242,419 A | 9/1993 | Kiner et al. | |
| 5,370,619 A | 12/1994 | Rossi | |
| 5,405,327 A | 4/1995 | Chen | |
| 5,445,620 A | 8/1995 | Haber et al. | |
| 5,531,705 A | 7/1996 | Alter et al. | |
| 5,688,240 A | 11/1997 | Novacek et al. | |
| 5,702,367 A | 12/1997 | Cover et al. | |
| 5,971,964 A | 10/1999 | Donaldson | |
| 6,015,438 A | 1/2000 | Shaw | |
| 6,066,115 A | 5/2000 | Chang Lai | |
| 6,090,077 A | 7/2000 | Shaw | |
| 6,090,078 A | 7/2000 | Erskine | |
| 6,183,440 B1 | 2/2001 | Bell | |
| 6,206,857 B1 | 3/2001 | Chen | |
| 6,221,052 B1 | 4/2001 | Caizza et al. | |
| 6,251,095 B1 | 6/2001 | Liu | |
| 6,530,903 B2 | 3/2003 | Wang et al. | |
| 6,979,314 B2 | 12/2005 | Hsieh et al. | |
| 2003/0093038 A1 | 5/2003 | Chiang | |
| 2003/0212368 A1 | 11/2003 | Shue et al. | |
| 2004/0087907 A1 | 5/2004 | Smith et al. | |
| 2004/0116854 A1 | 6/2004 | Abulhaj et al. | |
| 2004/0210198 A1 | 10/2004 | Shih | |
| 2004/0236283 A1 | 11/2004 | Tang | |
| 2004/0254529 A1 | 12/2004 | Fitzgerald | |
| 2005/0113751 A1 | 5/2005 | Chen | |
| 2005/0148931 A1 | 7/2005 | Juhasz | |
| 2006/0100577 A1 | 5/2006 | Shue et al. | |

FOREIGN PATENT DOCUMENTS

| | | |
|---|---|---|
| CA | 2183823 A1 | 2/1998 |
| CA | 2444988 A1 | 4/2004 |
| CA | 2459795 A1 | 9/2004 |
| EP | 0413414 A1 | 6/1990 |
| EP | 0498376 A1 | 2/1992 |
| EP | 1184049 B1 | 7/2001 |
| EP | 1438979 A1 | 12/2002 |
| EP | 1421963 A1 | 5/2004 |
| FR | 2667249 A1 | 4/1992 |
| FR | 2755614 A1 | 5/1998 |
| WO | 90/05555 A1 | 5/1990 |
| WO | 90/06148 A1 | 6/1990 |
| WO | 91/00751 A1 | 1/1991 |
| WO | 91/08788 A1 | 6/1991 |
| WO | 93/06880 A1 | 4/1993 |
| WO | 94/04207 A1 | 3/1994 |
| WO | 95/30445 A1 | 11/1995 |
| WO | 98/48869 A1 | 11/1998 |
| WO | 00/18466 A1 | 4/2000 |
| WO | 00/48651 A1 | 8/2000 |
| WO | 03/066144 A1 | 8/2003 |
| WO | 2004/045683 A1 | 6/2004 |
| WO | 2005/058398 A1 | 6/2005 |
| WO | 2006/029448 A1 | 3/2006 |
| WO | 2006/063377 A1 | 6/2006 |
| WO | 2006/096909 A1 | 1/2008 |

* cited by examiner

SAFETY SYRINGE WITH PLUNGER LOCKING MEANS

TECHNICAL FIELD

This invention relates to a safety syringe having a retractable needle for use in the medical or dental profession or in personal drug administration so that the physician, surgeon or other needle operator might be protected from injury by the needle after its use. In particular it relates to locking means for retaining the plunger to which the needle is attached, and hence the needle, in the retracted position.

BACKGROUND

The danger of injury and possible infection from the HIV or hepatitis B virus to medical practitioners using needles in the normal course of their business is well documented.

Further, persons who are in the habit of administering drugs to themselves run a severe risk of contacting either of the specified viruses, or indeed contacting other viruses if a needle, once used, is reused in an unsterilised form.

There have been many proposals aimed at reducing the number of so-called needle-stick injuries and various attempts have been made to provide a safe system for disposal of such needles once used, but such prior proposals have had deficiencies.

Many solutions to the foregoing problems provide for retractable needles. One of the major disadvantages in many previous proposals is that the syringe although rendered initially safe by having the needle retracted, does not usually provide means for preventing further access to the needle. In other words, the plunger may be depressed again causing the needle to re-emerge from the barrel of the syringe, or in some other instances may be withdrawn altogether form the barrel of the syringe thereby gaining access to the needle.

OBJECT OF THE INVENTION

It is an object of the present invention to provide a syringe which to some extent solves or at least ameliorates some or all of the foregoing disadvantages by employing a retractable surgical needle, and for permanently storing that surgical needle, once used, in a substantially safe manner. In particular, the present invention provides for a positive locking facility to prevent the plunger, to which the withdrawn needle is attached, from being reactivated or even withdrawn altogether, once the syringe is rendered safe by having the needle retracted. At the very least the invention provides an alternate means for accommodating the needle of a used syringe to protect against accidental injury arising from unwanted contact with the exposed needle once the syringe has been used.

Although the following description generally refers to a syringe of conventional size, no such limitation is intended thereby, and reference to a syringe is meant to encompass any other needle/syringe combination or needle alone including slimline syringes, where, by suitable adaptation, the invention may also be usefully applied.

DISCLOSURE OF THE INVENTION

According to the present invention there is provided a safety syringe having a retractable needle facility incorporated therein, the syringe comprising a barrel and plunger and needle assembly, wherein the needle is caused to retract into the barrel of the syringe upon completion of injection once it has been used, by means of engagement between the needle assembly and the end of the plunger, and wherein locking means is provided in the body of the syringe to engage the plunger once it is retracted after use, so that the syringe is rendered incapable of being used further.

In this sense, rendering the syringe incapable of further use means that neither can the plunger be pushed down again to reactive the needle, nor can it be removed altogether from the barrel of the syringe to gain access to the needle.

Preferably a region of weakness is provided in the plunger, located on the shaft of the plunger in the vicinity of where it extends from the end of the syringe body when fully withdrawn, so that after the needle is retracted into the body of the syringe, and the plunger is engaged with the locking means, the plunger is broken off so that it cannot be depressed again, or readily removed by gripping it and exerting force, thereby further assisting in rendering the syringe incapable of being used again.

It will be understood that whilst the invention is arguably improved by the ability to break off the plunger as well, it should be appreciated that this is an extra step and one that some users might ignore. Therefore it is preferable that the locking means be of sufficient resistance to prevent the plunger from being depressed or removed so that it does not matter that the plunger is broken off. In other words, even before the plunger is broken off, the present invention envisages that the syringe will be rendered ineffective against ether deliberate or even accidental re-use as night occur if the syringe were knocked as it was being placed on a table for example.

Preferably the locking means is provided by a bush located in the end of the syringe barrel from which the plunger extends.

The bush may be a split bush or a solid bush, although it has been found particularly advantageous to have a split in the bush for ease of fitment to the barrel. A split bush has been found to provide easier fit during manufacture of the syringe, since the bush needs to be fitted after the plunger is inserted in the barrel. By virtue of the split provided the bush can be made to fit around the shaft of the plunger and can be made to reduce in diameter when being pressed into the barrel and will snap fit into the internal region of the barrel designed to accommodate it.

The bush may utilise any one of a variety of methods to engage the plunger once it has engaged the needle and caused it to be withdrawn into the barrel of the syringe, including, but not necessarily limited to twisting or pulling the plunger through or into the bush as the case may be. In those bushes where a twisting motion is required, the bush may be a twist-lock bush or a threaded bush or may be a luer-lock bush. Alternatively in embodiments where a pull motion is required, the bush may be a pull-lock bush or snap-lock bush. Examples of these bushes are illustrated in the accompanying drawings and discussed below in relation to the description of the respective drawings.

As mentioned above, the bush is preferably pressed into the barrel after the plunger is inserted. A variety of locking options are also available to retain the bush in the barrel. Any combination of locking mechanism to retain the plunger in the locking bush may be coupled with any one of the such means by which the bush itself is retained in the barrel of the syringe.

It will be appreciated that there are many different means available by which the bush can be used to lock the plunger and these are contemplated as being within the scope of the invention.

It is also preferred that a vertical or longitudinal protrusion within the end of the barrel where the bush is inserted, is provided whereby the bush may be prevented from turning, particularly in those cases where a split bush is utilised or where a twisting action is required to lock the plunger in the bush.

Furthermore it is preferable that the plunger itself is provided with a flange about its distal end to prevent it from being pulled right through the locking means. In this way the syringe will not only be rendered ineffective against the plunger being depressed again, but also rendered safe in that the plunger cannot be removed altogether. Thus, once the plunger locks into the bush, neither the plunger nor the bush itself may be withdrawn to otherwise gain access to the needle located within the barrel after it has been withdrawn into the barrel.

Thus, with advantage, locking of the plunger in the bush is preferably improved by a flange located on the plunger, preferably located just above the piston region of the plunger, allowing the plunger to be thus locked against the bottom of the bush, preventing the plunger from being entirely withdrawn.

By providing a break point in the plunger, as discussed above, it will also prevent or at least minimise the possibility of further tampering, especially preventing access to the plunger in a way which allow it to be forced back into the barrel or gripped for removal by excessive force.

Thus for example one preferred embodiment utilises a twist lock feature including corresponding threaded regions in the barrel of the syringe and on the plunger, so that after an injection the plunger is withdrawn and locked in position by twisting the plunger to engage the corresponding threaded portions.

Alternatively the locking means is provided by a twist lock feature including a twist lock bush having helix grooves therein located in the barrel of the syringe and corresponding lugs located on the plunger for engagement in the helix grooves, so that after an injection, the plunger is withdrawn and locked in position by twisting the plunger to engage the lugs in the corresponding helix grooves.

Again, as an alternative, the locking means may be provided by a twist lock feature including a twist lock bush having helix grooves therein located in the barrel of the syringe and lugs located on the plunger for engagement in the helix grooves, so that after an injection the plunger is withdrawn and locked in position by twisting the plunger to cause the lugs to move through the corresponding helix grooves and pass completely through the bush.

Preferably in this embodiment, a permanent lock facility is provided in the form of a ramp or other protrusion to prevent the lugs from returning through the grooves of the bush and hence preventing the plunger from passing back through the bush into the barrel of the syringe.

More preferably however, it has been found that a locking bush with a simple flange arrangement is both easy to produce and effective. In this arrangement a flange around is the internal perimeter of the bush allows a corresponding flange on the plunger to pass in one direction, but by virtue of the shape of the flanges prevents its return. In combination with an additional flange on the plunger as described above, the plunger is prevented from being drawn right through the bush providing an effective lock against movement in either direction.

Instead of a flange around the entire internal perimeter of the bush, it has been found that a pair of fingers function just as efficiently. Movement of the fingers to allow the first flange of the plunger to pass can be achieved by shaping the internal region of the barrel to allow the fingers to bend back as the flange of the plunger passes, snapping back by virtue of the resilience once the first flange has passed.

Although much of the following description refers to a particular safety syringe having a retractable needle with certain features, it will be understood that the twist locking mechanism may be utilised with any syringe having any form of retractable needle facility.

The invention finds application for example in one broad embodiment which provides a syringe having a retractable needle facility incorporated therein, so that in a first storage position prior to use, the needle is safely enclosed within the body of the syringe and in a second in use position, the needle is caused to extend from the body of the syringe so as to function as a useful needle and syringe combination in known fashion, and wherein the needle is then caused to retract again into the body of the syringe, once it has been used, so as to return it to the first storage position; the syringe comprising a body and plunger, wherein the plunger has means associated with the end thereof contained within the body of the syringe to releasably engage a boss of the needle located in the syringe body so as to retain the needle within the syringe body in the first storage position, and wherein the body of the syringe has means located at the end thereof opposite to where the plunger extends from the body for releasably retaining the needle boss in the second in use position so that the needle extends from the syringe body, the plunger being used to bring the needle boss into engagement with the end of the syringe body; the plunger then being able to be disengaged from the needle boss so as to enable the plunger to be withdrawn and thereby take in fluid into the syringe and then to be used to inject same into a patient in known fashion; and when upon completion of injection, and the needle having been withdrawn from the patient, the plunger is once again brought into engagement with the needle boss and withdrawn so as to cause the needle boss to be released from the end of the syringe body so that the needle is once again retracted into the body of the syringe, the needle remaining attached to the end of the plunger.

Alternatively, the needle assembly may be such that in the initial position, the needle is already extended, ready for use, or may be gland arrangement to which a replaceable needle may be fitted, the needle in either case being protected by a suitable sheath or cover prior to use, so that the end of the plunger only comes into contact with the needle assembly or gland as the case may be at the end of the injection, at which point engagement between the plunger and the assembly or gland is achieved, so that the assembly or gland is withdrawn together with the needle itself into the barrel upon retraction of the plunger.

The plunger is then caused to engage with the locking bush and preferably snapped off at the break point to render the syringe safe and ineffective against further use.

The invention is thus of particular benefit in that the needle is not only safely retracted after use, but is locked in that position by means of the locking bush.

Snapping off the plunger (if provided) also renders the syringe both ineffective for subsequent use as well as providing additional safety in that there is no means by which the needle can be caused to re-emerge or caused to extend from the syringe body.

BRIEF DESCRIPTION OF THE DRAWINGS

The invention may be better understood from the following non-limiting description of preferred embodiments, in which.

DETAILED DESCRIPTION OF THE DRAWINGS

Figure 1:
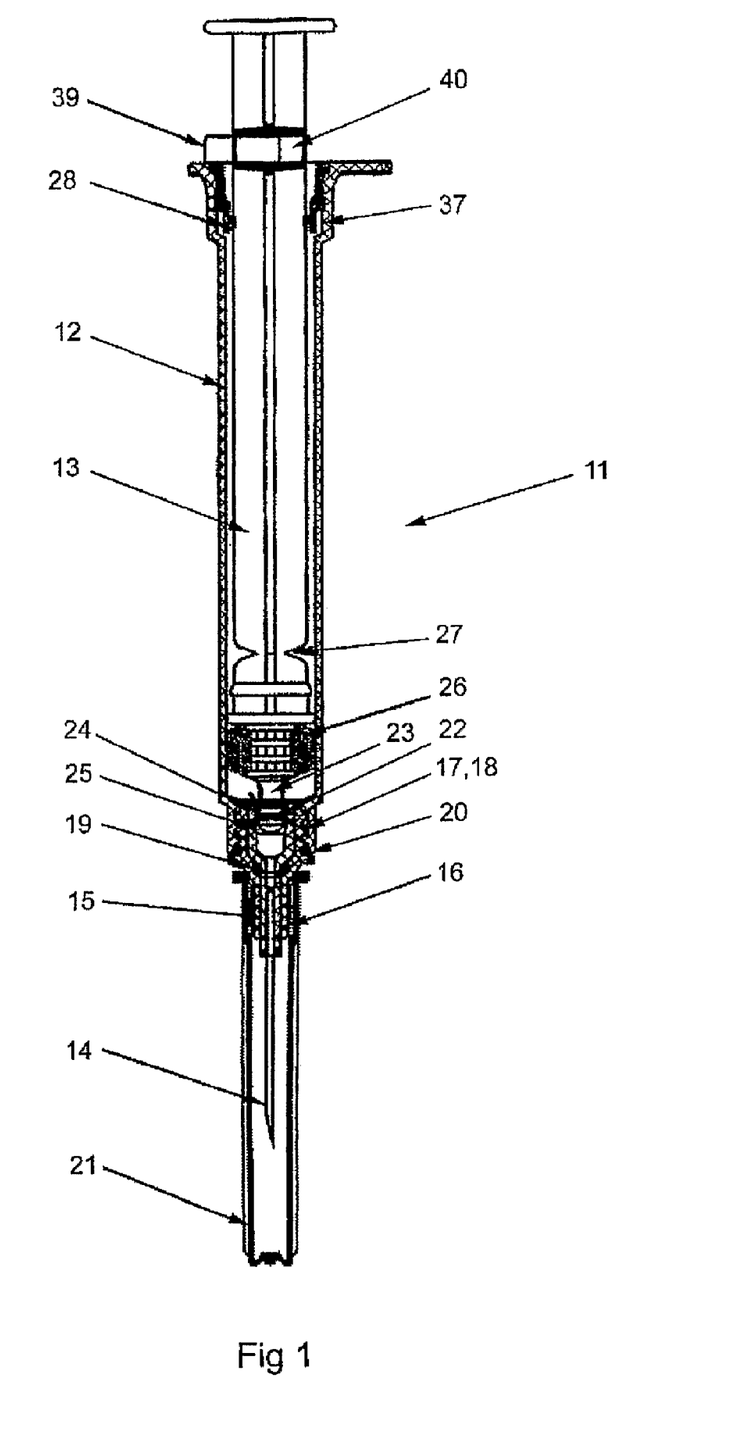
FIG. 1 is a cross sectional view of one embodiment of the invention utilising a locking bush according to one aspect of the invention in which a snap lock split bush is utilised to retain the plunger after use.

Referring generally to FIGS. 1 to 8 and especially FIG. 1, there is shown a syringe according to one aspect of the invention generally referenced 11, which comprises a syringe body or barrel 12, a plunger 13 slideable therein and a needle 14. The needle 14 is provided with a hub 15. The plunger 13 and barrel 12 are shown separately in FIGS. 2 and 3 for greater clarity.

The needle hub 15 is located by interference fit in a gland 16 which in this embodiment is screwed into the end of the barrel 12 utilising an internal female thread 17 on the inside of the end of the barrel 12, and a male thread 18 on the gland 16. In this embodiment the needle assembly comprising the needle and hub 14/15 and gland 16 may be replaced or exchanged (or indeed fitted) prior to use of the syringe so to provide flexibility of choice with respect to needle gauge for example.

It will also be appreciated that in the alternative, the gland 16 could be screwed onto the outside of the barrel 12, for example in slimline syringes. These embodiments allow for replacement of the needle assembly in a so-called exchange needle. On the other hand, the needle and hub 14/15 may be utilised directly in the end of the barrel 12 in integral arrangement, without a gland 16, in other embodiments of the invention, where there is no need to exchange the needle 14.

A small seal 19 is provided to seal between the needle hub 15 and gland 16, whilst a second larger seal 20 is provided to seal between the gland 16 and the barrel 12

The needle 14 is protected by a cover 21 prior to use.

Figures 2, 3:
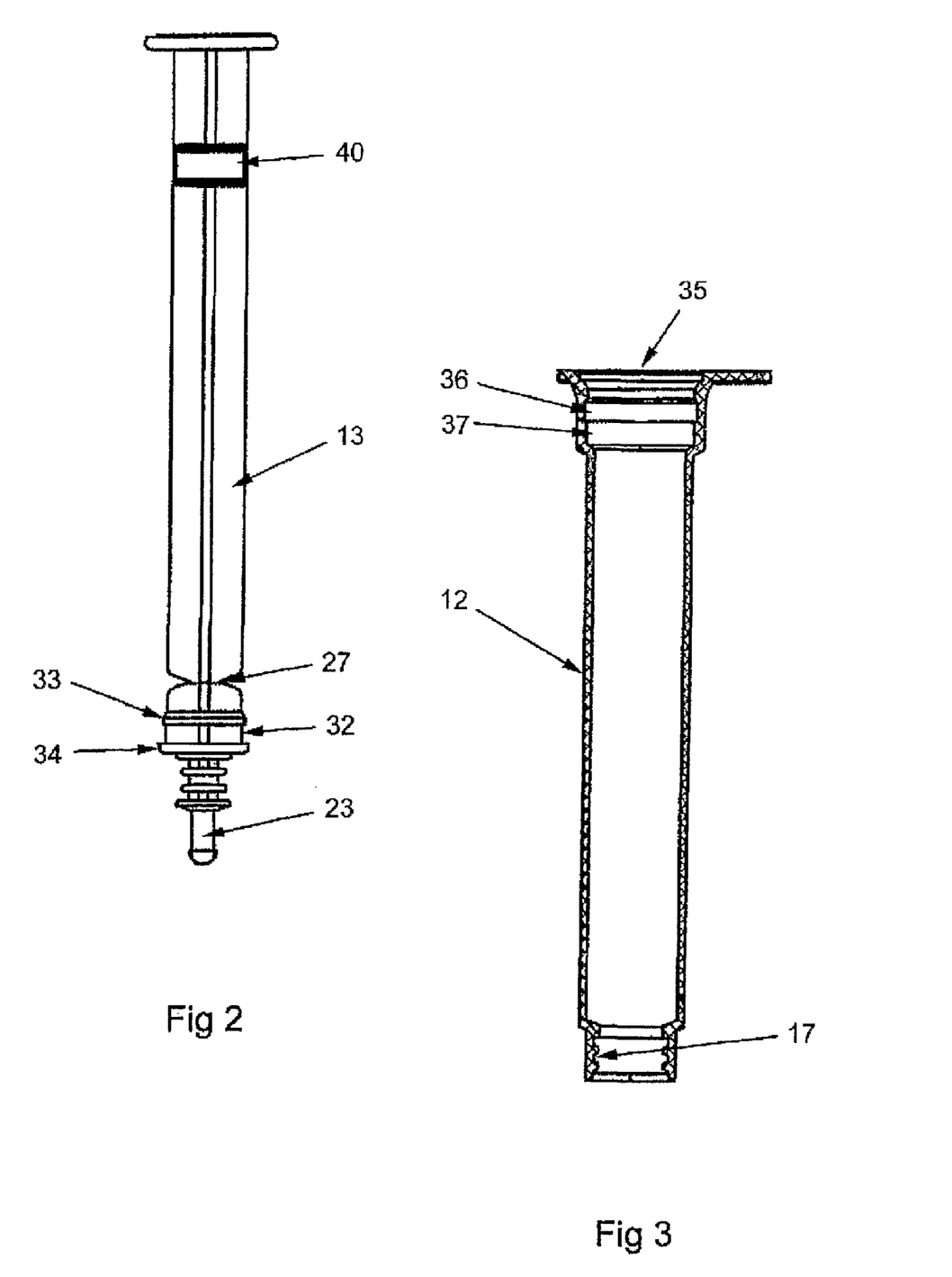
FIG. 2 is a cross sectional view of the plunger utilised in the embodiment of FIG. 1.
FIG. 3 is a cross sectional view of the barrel utilised in the embodiment of FIG. 1.
Figure 4:
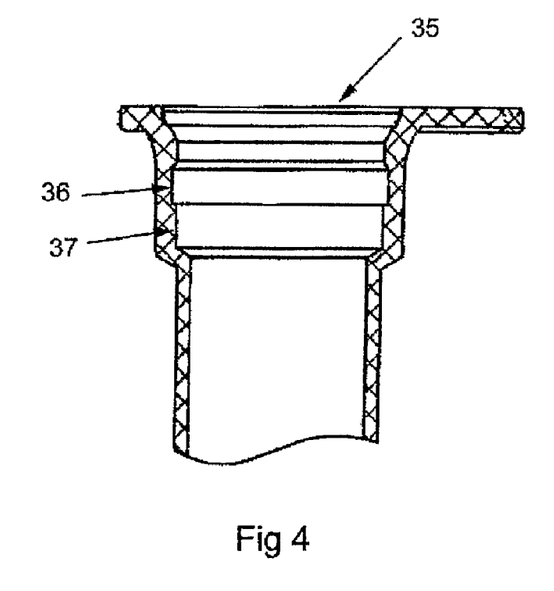
FIG. 4 is a cross sectional view of the end of the barrel of FIG. 3 to which a locking bush may be fitted.

Plunger 13 is provided with clip means 22 located on a stem 23 at the end of the plunger 13. The clip has a barb 24 which engages with the inner region 25 of the needle hub 15 when the plunger 13 is brought into contact with the needle hub 15 at the end of the injection.

Plunger 13 is also provided with a piston region 26 about its lower periphery which seals against the inside of the syringe body 12, when inserted therein.

A break groove or weaker region 27 is provided at a suitable location on the plunger 13, so that it may be broken off after it has retracted the needle 14 into the barrel of the syringe 12, that is to say, after use as described below.

A locking bush 28 is located in the upper region of the barrel 12.

Details of the locking bush 28 and relevant portions of the syringe 11 pertaining to its use are illustrated in detail in FIGS. 4 to 8.

Figures 5, 6, 8:
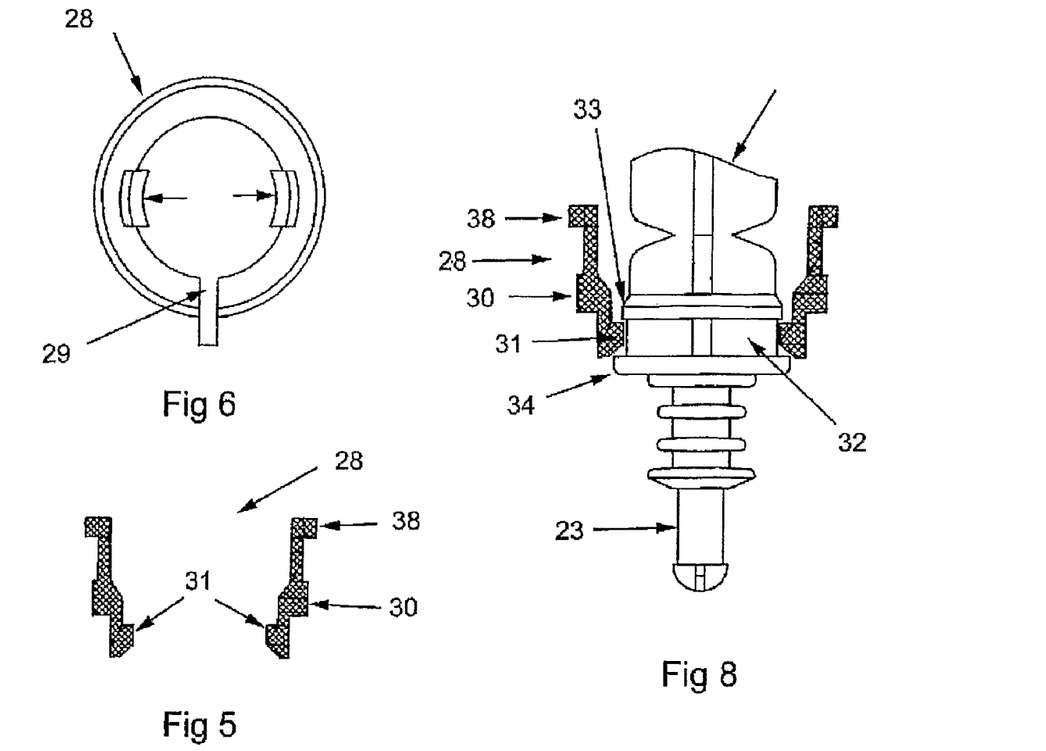
FIG. 5 is a cross sectional view of a preferred embodiment of a locking bush for use with the syringe and its components as illustrated in FIGS. 1 to 4.
FIG. 6 is a plan view of the locking bush of FIG. 5.
FIG. 8 is a cross sectional view of the end of the plunger and clip of the previous figures, after engagement has taken place.

Locking bush 28 has a split region shown diagrammatically at 29 in FIG. 6 for ease of fitment of the bush 28 to the barrel 12. A flange 30 is located about its periphery and a pair of fingers 31. depend from the bush 28 for mating with a corresponding circumferential groove region 32 located between circumferential flanges 33 and 34 located near the end region of the plunger 13. The flange 33 and fingers 31 are suitably ramped on one side to provide ease of passing, but have faces on the other side which are effectively parallel with each other, so as to prevent return.

The profile of the inner region 35 of the end of the barrel 12 similarly allows for ease of fitment and retention of the bush 28 therein specifically by providing a groove 36 into which flange 30 locates for mating engagement with appropriate ramping where required to assist in fitment. In particular a recess 37 is provided behind the fingers 31 of the bush 28 when it is in place (as shown in FIG. 1), so that the fingers 31 can deform as the end of the plunger 13 engages therewith.

A flange 38 is also located about the periphery of the bush to strengthen it and assist in alignment of the bush 28 when being fitted to the barrel 12.

Figure 7:
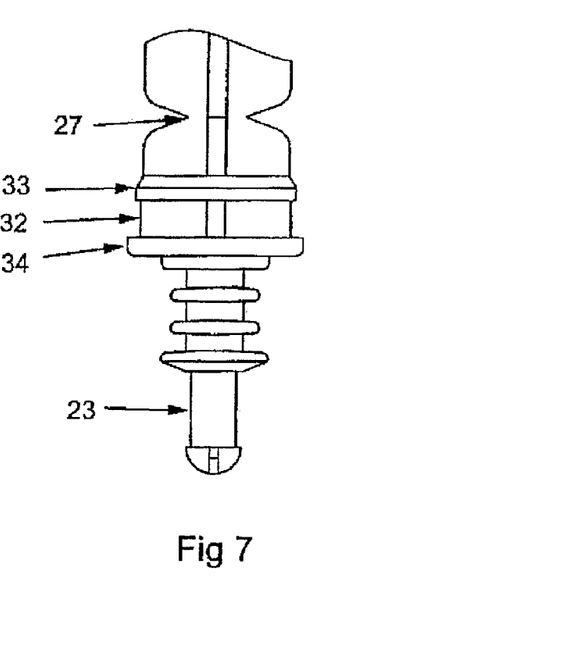
FIG. 7 is a detailed cross sectional view of the end of the plunger of FIG. 2, which engages with the clip of FIGS. 5 and 6 when the plunger is retracted after it has engaged and retracted the needle (not shown)

Specifically, the first flange 33 is able to pass the fingers 31 by pushing them into the recess 37 as that region of the plunger 13 passes the fingers 31 of the bush 28. The second flange 34 is provided with a greater diameter than that of flange 33 so as to be prevented from passing the fingers 31, thereby locking the plunger 13 when the fingers 31 thus engage in the groove 36. The plunger 13 can the be neither pulled further through the bush 28 by virtue of flange 34, nor can it be depressed again by virtue of flange 33.

Returning to FIG. 1, a pin 39 is also located in hole 40 in the upper region of plunger 13. Pin 39 acts as a depth stop to prevent accidental engagement of the plunger 13 with the needle hub 15 prior to use. When the syringe is about to be used, the pin 39 can be easily depressed so as to allow full travel of the plunger 13 in the barrel 12.

Thus in use, after an injection has been completed, the plunger 13 is pushed home to engage with the needle hub 15. The plunger 13 with needle 14 engaged is then retracted, the needle 14 being thus withdrawn into barrel 12, the plunger 13 being then drawn fully back so as to engage with the locking bush 28 by means of flanges 33 and 34 preventing the plunger from moving in either direction once the fingers 31 have engaged in the groove 36 located therebetween.

The plunger 13 is then snapped off at break point 27. With the plunger 13 disabled and the needle 14 retracted inside the body 12 of the syringe 11, it is rendered totally useless and may then be disposed of safely.

Figure 9:
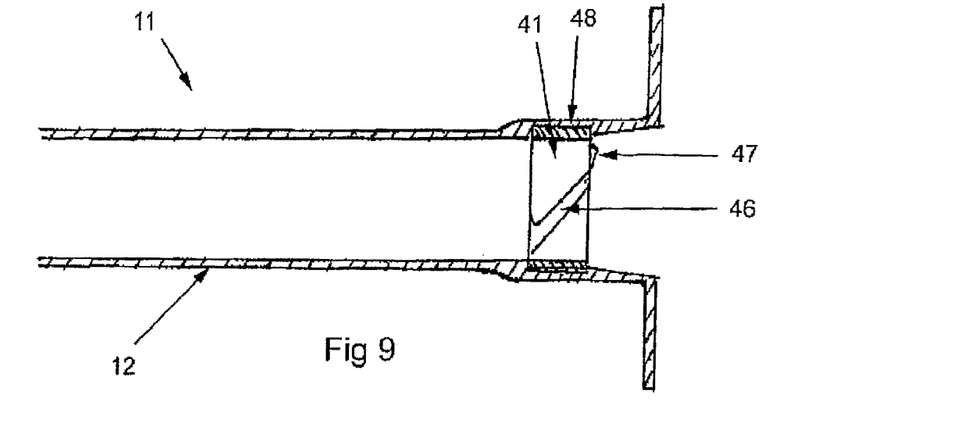
FIG. 9 is a cross sectional view of a syringe barrel utilising a twist lock bush being an alternative embodiment of the invention to that illustrated in FIGS. 1 to 8.
Figure 10:
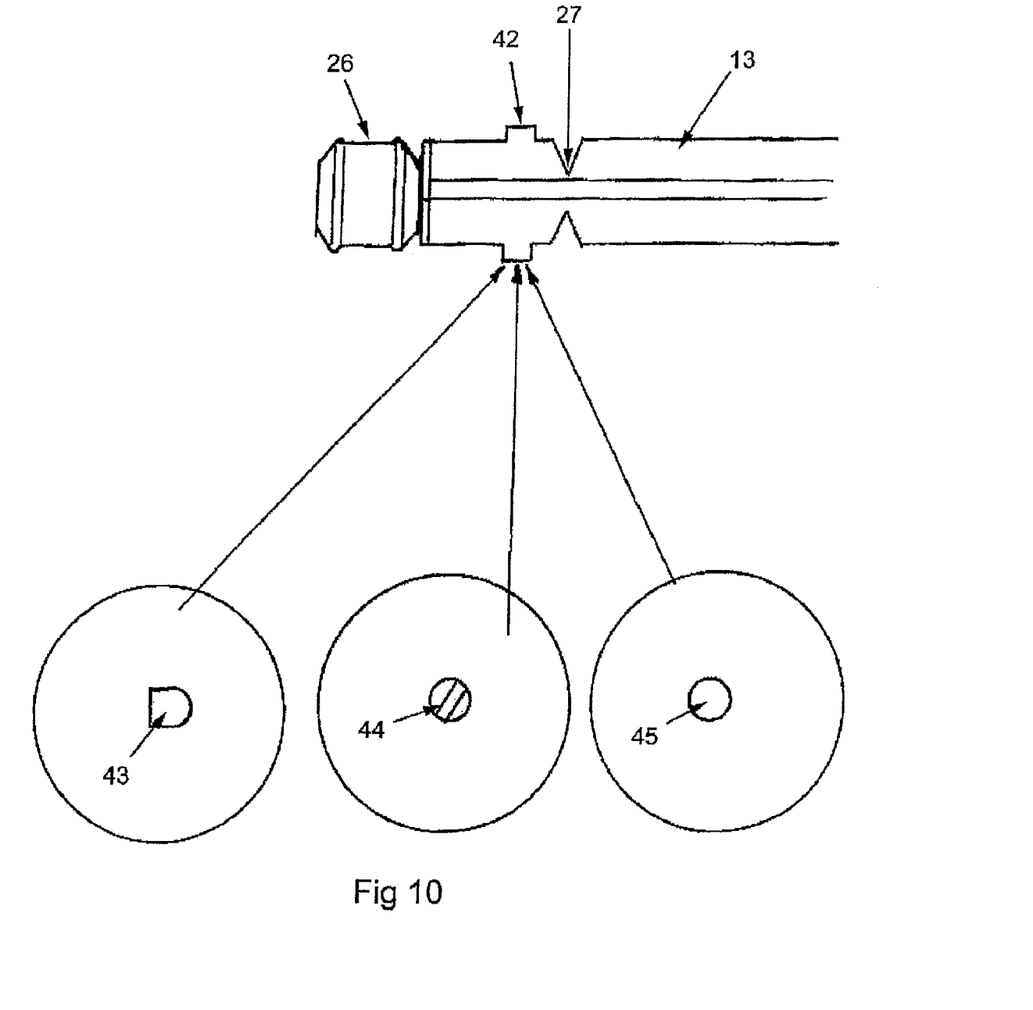
FIG. 10 is a detailed cross sectional view of a plunger for use with the twist lock bush of FIG. 9.

FIGS. 9 and 10, where like features common to FIGS. 1 to 8 are referenced with the same reference numerals, specifically show in detail an alternate embodiment of the invention in the form of a twist lock bush 41 and corresponding plunger 13 for use therewith. This combination may for example be used in any syringe including that of FIG. 1, where a locking mechanism is required to retain a retracted needle 14 located on the end of a plunger 13, and whereby it is desired to render the syringe 11 completely unusable after use by locking the plunger 13 and breaking it off at break point 25 and hence leaving the needle 14 encased in the barrel 12 of the syringe 11 and otherwise inaccessible.

The plunger 13 is provided with lugs 42 which may be of any suitable cross sectional shape. Three particular sections are shown in detail at 43, 44, 45, being respectively round entrance with flat base, thread segment and simple round. In this embodiment lugs 42 are located on the ribs of the plunger 13, whereas the corresponding feature of the previous embodiment, namely flange 33 was in that embodiment formed circumferentially (and described thus) about the plunger 13, rather than being an extension of a rib element of the plunger 13

The bush 41 can be split to wrap around the plunger 13 as in the previous embodiment. Alternatively it may be solid and screwed over the plunger 13 prior to fitting the piston 26 thereto. The bush 41 has two helix internal grooves 46 to feed the lugs 42 as the plunger 13 is twisted through the bush 41. When the lugs 42 come through the bush 41 they rise over the permanent lock 47 and the plunger 13 is thereby locked within the barrel 12. With the plunger 13 locked, the piston 26 is displaced jamming it within the barrel 12. As the piston 26 is reduced in depth it expands in diameter. The twist lock bush 41 is held in the barrel 13 within groove 48 as shown.

FIGS. 11 through 15 show a variety of means by which locking bushes 41 may be utilised with corresponding plungers 13. Feature already described utilise the same reference numerals for convenience.

Figure 11A:
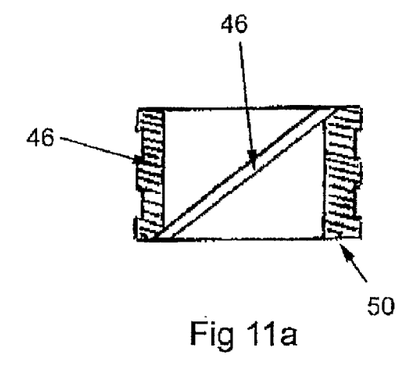
FIGS. 11a/11b to FIGS. 15a/15b schematically show pairs of bushes and corresponding plungers according to various alternative embodiments.
Figure 11B:
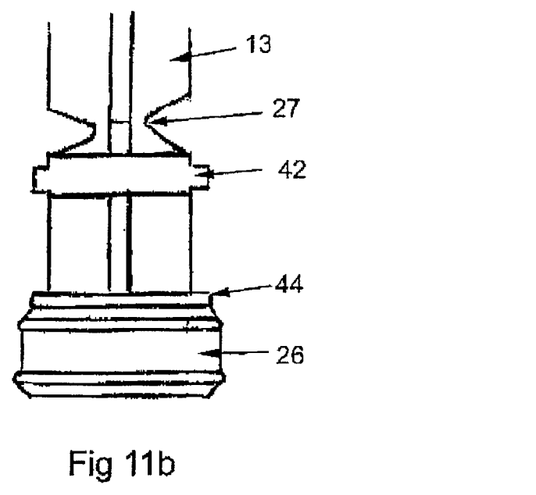

FIGS. 11a,11b show a locking bush 41/plunger 13 combination in which generally the bush 41 has two spiral grooves 46. The two lugs 42 on the plunger 13 engage the spiral grooves 46 when the plunger 13 is retracted locking the plunger 13 as it is twisted. Locking takes place when the lugs 42 climb out the top of the bush 41, at the same time the flange 49 located above the piston 26 is locked on the base 50 of the twist-lock bush 41, preventing movement of the plunger 13 either up or down.

Figure 12A:
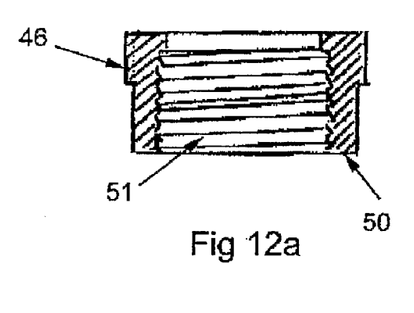
Figure 12B:
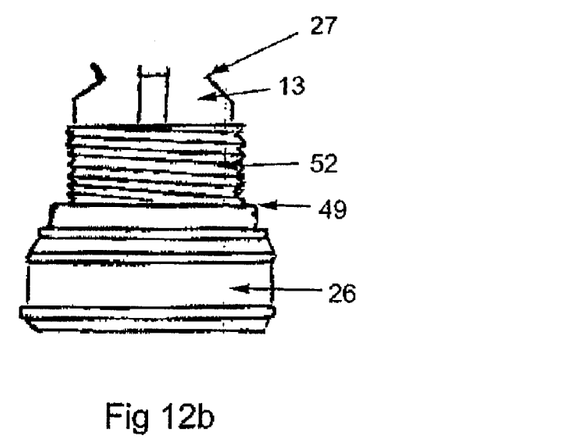

FIGS. 12a,12b show a bush 41 which has a thread 51 (which may be any thread). As the plunger 13 is retracted and the thread 51 is engaged with corresponding thread 52 on the plunger 13, rotation will stop when the shoulder 53 in the bush 41 is reached. At the same time the flange 49 above the piston 26 locks onto the bottom 50 of the threaded bush 41.

Figure 13A:
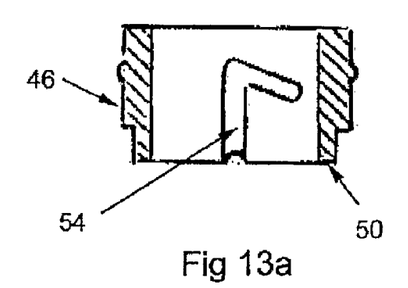
Figure 13B:
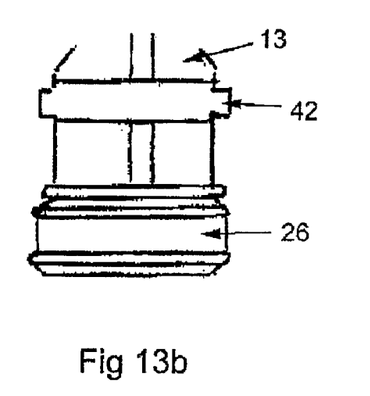

In FIGS. 13a,13b there is depicted a bush 41 which is a pull-lock bush. The bush 41 has two grooves 54 on the inside of the bush 41 as shown. Locking takes place as the plunger 13 is retracted through the grooves 54 and is twisted, the lugs 42 on the plunger 13 mating with the internal grooves 54 in the bush 41. The lugs 42 are thus allowed to settle in the lower horizontal grooves 55 in bayonet fitting fashion. At the same time, the flange 49 above the piston 26 again locks onto the bottom 50 of the pull lock bush 41.

Figure 14A:
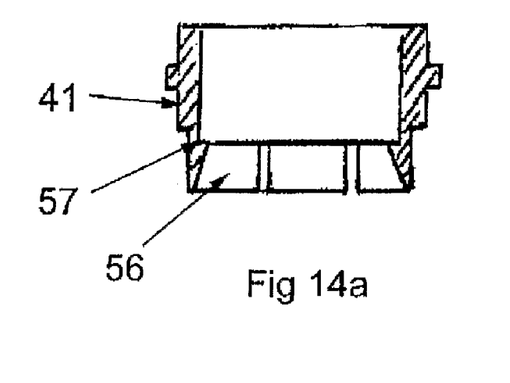
Figure 14B:
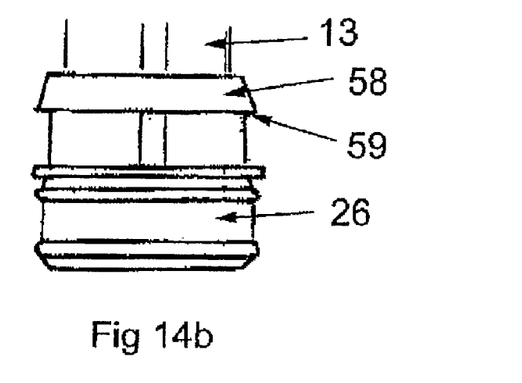

In FIGS. 14a,14b there is shown a snap-lock bush 41 in which the inside has a locking taper fingers 56 and a step 57. As the plunger 13 is retracted through the snap lock tapered flange 58 on the plunger 13, it engages the tapered locking fingers 56 by spreading them to allow the plunger 13 through. The tapered fingers 56 snap back around the plunger taper 58 and the two steps, one 59 on the plunger 13 and the other 57 at the top of the fingers 56 inside the bush 41, lock thereby making it impossible for the plunger 13 to be pushed down.

Figure 15A:
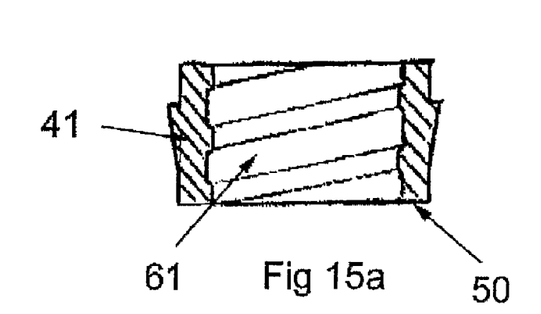
Figure 15B:
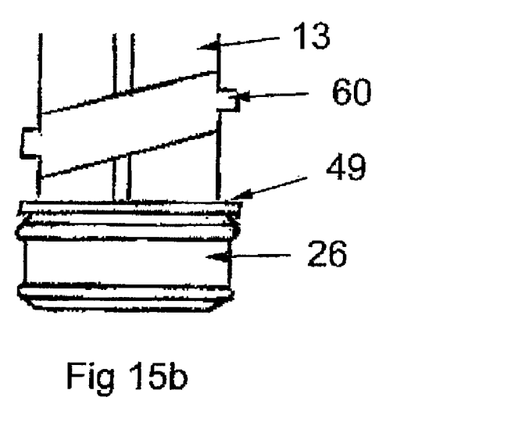

FIGS. 15a,15b depict a plunger 13 which has two flutes 60 similar to a needle hub which engage the luer-lock design 61 within the bush 41. As the twisting of the plunger 13 takes place, the plunger 13 travels up locking between the flange 49 above and the piston 26 and the bottom 50 of the bush 41.

In each of the foregoing cases the plunger 13 is broken off at break point 27 thereby preventing any unauthorised or accidental re-use of the syringe 11.

Figures 16, 17:
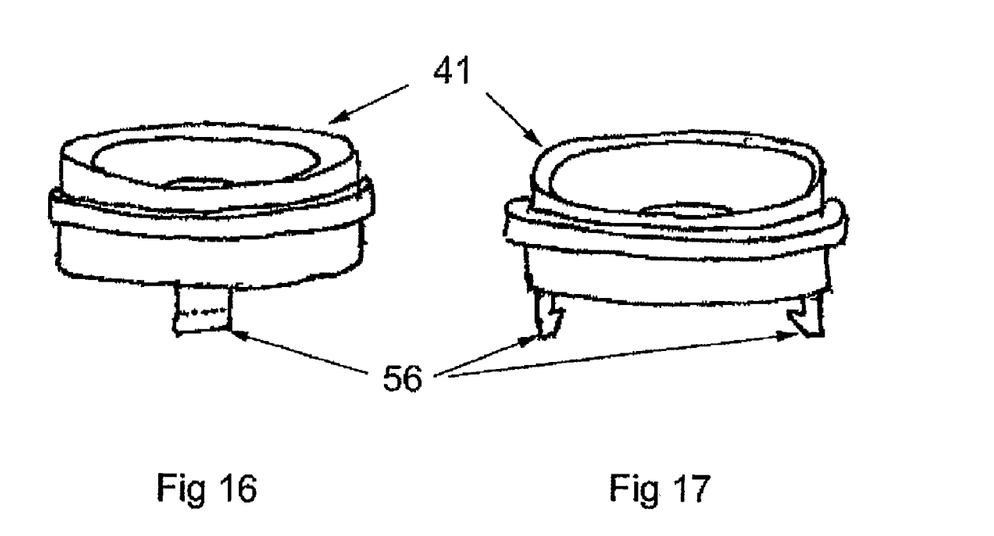
FIGS. 16 and 17 show from two perspectives a simplified bush similar to that of FIGS. 5 and 6 according to a yet further embodiment of the invention.

A simplified version of the snap-lock bush depicted in FIGS. 14,14b is depicted in FIGS. 16 and 17, where the fingers 51 can be as little as two. Although not shown, the bush 41 may also be split to allow for ease of assembly, so that the distal end of the plunger 13 is first pushed into the barrel 12 of the syringe 11. The bush 41, can then be placed around the plunger 13 during assembly of the syringe 11 and pushed into position before the plunger 13 is made to rest at its starting position, prior to but ready for use.

It will be appreciated by those skilled in the art that many modifications and variations may be made to the embodiments described herein without departing from the spirit or scope of the invention.

Throughout the specification the word "comprise" and its derivatives are intended to have an inclusive rather than exclusive meaning unless the context requires otherwise.

The invention disclosed herein has utility in that provides an alternate means for a safety syringe having a retractable needle facility which can be rendered useless after an injection by locking the plunger and breaking it off

The invention claimed is:

1. A safety syringe having a retractable needle facility incorporated therein, the syringe comprising a barrel and plunger and needle assembly, wherein the needle is caused to retract into the barrel of the syringe upon completion of injection once it has been used, by means of engagement between the needle assembly and the end of the plunger, and wherein locking means is provided in the body of the syringe to engage the plunger once it is retracted after use, so that the syringe is rendered incapable of being used further, the locking means provided by a split bush located in the end of the syringe barrel from which the plunger extends and in which the bush is fitted after the plunger is inserted in the barrel and pressed into position in the barrel, wherein the split is made to fit around the shaft of the plunger and is made to reduce in diameter when so pressed into the barrel, and engages by snap fit in the internal region of the barrel and the locking means is provided by a bush having two spiral grooves, which mate with two lugs on the plunger which engage the spiral grooves when the plunger is retracted locking the plunger as it is twisted.

2. A safety syringe according to claim 1 in which the syringe incapable of further use in that the plunger cannot be pushed down again to reactive the needle, nor can it be removed altogether from the barrel of the syringe to gain access to the needle.

3. A safety syringe according to either claim 1 wherein a region of weakness is provided in the plunger, located on the shaft of the plunger in the vicinity of where it extends from the end of the syringe body when fully withdrawn, so that after the needle is retracted into the body of the syringe, and the plunger is engaged with the locking means, the plunger may be broken off so to render the syringe incapable of being used again.

4. A safety syringe according to claim 1 in which the bush is pressed into the barrel after the plunger is inserted.

5. A safety syringe according to claim 1, in which any suitable locking mechanism to retain the plunger in the locking bush is coupled with any suitable means by which the bush itself is retained in the barrel of the syringe.

6. A safety syringe according to claim 1 in which a vertical or longitudinal protrusion within the end of the barrel where the bush is inserted, is provided whereby the bush is prevented from turning.

7. A safety syringe according to claim 1 in which the plunger is provided with a flange about its distal end to prevent it from being pulled right through the locking means.

8. A safety syringe according to claim 7 in which the plunger is able to be locked against the bottom of the bush, preventing the plunger from being entirely withdrawn.

9. A safety syringe according to claim 1 in which the bush utilizes twisting or pulling of the plunger through or into the bush.

10. A safety syringe according to claim 9 in which the bush is a twist-lock bush and the twisting is provided by a threaded bush or a luer-lock bush.

11. A safety syringe according to claim 9 in which the syringe utilizes a twist lock feature including corresponding threaded regions in the barrel of the syringe and on the plunger, so that after an injection the plunger is withdrawn and locked in position by twisting the plunger to engage the corresponding threaded portions.

12. A safety syringe according to claim 9 in which the locking means is in the form of a bush having a thread, and wherein as the plunger is retracted and the thread is engaged with a corresponding thread on the plunger, rotation will stop when the shoulder in the bush is reached, whilst at the same time the flange above the piston locks onto the bottom of the threaded bush.

13. A safety syringe according to claim 1 in which the bush is a pull-lock bush or snaplock bush.

14. A safety syringe according to claim 13 in which the locking means has a permanent lock facility provided in the form of a ramp or other protrusion to prevent the lugs from returning through the grooves of the bush and hence preventing the plunger from passing back through the bush into the barrel of the syringe.

15. A safety syringe according to claim 14 in which a pair of fingers cooperates with the first flange of the plunger allowing it to pass by virtue of the shaping of the flanges in ramped arrangement and by the shaping of the internal region of the barrel to allow the fingers to bend back as the flange of the plunger passes, snapping back by virtue of the resilience once the first flange has passed.

16. A safety syringe according to claim 14 in which the locking bush is a snap-lock bush in which the inside has a locking taper and a step, so that as the plunger is retracted through the snap lock tapered flange, it engages the tapered locking fingers by spreading them to allow the plunger through, and wherein the tapered fingers snap back around the plunger taper and the two steps, one on the plunger and the other at the top of the fingers inside the bush, lock thereby making it impossible for the plunger to be pushed down.

17. A safety syringe according to claim 1 having a retractable needle facility incorporated therein, so that in a first storage position prior to use, the needle is safely enclosed within the body of the syringe and in a second in use position, the needle is caused to extend from the body of the syringe so as to function as a useful needle and syringe combination in known fashion, and wherein the needle is then caused to retract again into the body of the syringe, once it has been used, so as to return it to the first storage position; the syringe comprising a body and plunger, wherein the plunger has means associated with the end thereof contained within the body of the syringe to releasably engage a boss of the needle located in the syringe body so as to retain the needle within the syringe body in the first storage position, and wherein the body of the syringe has means located at the end thereof opposite to where the plunger extends from the body for releasably retaining the needle boss in the second in use position so that the needle extends from the syringe body, the plunger being used to bring the needle boss into engagement with the end of the syringe body; the plunger then being able to be disengaged from the needle boss so as to enable the plunger to be withdrawn and thereby take in fluid into the syringe and then to be used to inject same into a patient in known fashion; and when upon completion of injection, and the needle having been withdrawn from the patient, the plunger is once again brought into engagement with the needle boss and withdrawn so as to cause the needle boss to be released from the end of the syringe body so that the needle is once again retracted into the body of the syringe, the needle remaining attached to the end of the plunger.

18. A safety syringe according to claim 17 wherein the needle assembly is such that in the initial position, the needle is already extended, ready for use, or may be gland arrangement to which a replaceable needle is fitted, the needle in either case being protected by a suitable sheath or cover prior to use, so that the end of the plunger only comes into contact with the needle assembly or gland as the case may be at the end of the injection, at which point engagement between the plunger and the assembly or gland is achieved, so that the assembly or gland is withdrawn together with the needle itself into the barrel upon retraction of the plunger.

19. A safety syringe according to claim 17, wherein after the plunger has been caused to engage with the locking bush it is then snapped off at the break point to render the syringe safe and ineffective against further use.

20. A safety syringe according to claim 14 in which a flange is located around the internal perimeter of the bush allows a corresponding flange on the plunger to pass in one direction, but by virtue of the shape of the flanges prevents its return and wherein in combination with an additional flange on the plunger as described above, the plunger is prevented from being drawn right through the bush providing an effective lock against movement in either direction.

21. A safety syringe having a retractable needle facility incorporated therein, the syringe comprising a barrel and plunger and needle assembly, wherein the needle is caused to retract into the barrel of the syringe upon completion of injection once it has been used, by means of engagement between the needle assembly and the end of the plunger, and wherein locking means is provided in the body of the syringe to engage the plunger once it is retracted after use, so that the syringe is rendered incapable of being used further, the locking means provided by a split bush located in the end of the syringe barrel from which the plunger extends and in which the bush is fitted after the plunger is inserted in the barrel and pressed into position in the barrel, wherein the split is made to fit around the shaft of the plunger and is made to reduce in diameter when so pressed into the barrel, and engages by snap fit in the internal region of the barrel and the syringe utilizes locking means in the form of a twist lock feature including a twist lock bush having helix grooves therein located in the barrel of the syringe and corresponding lugs located on the plunger for engagement in the helix grooves, so that after an injection, the plunger is withdrawn and locked in position by twisting the plunger to engage the lugs in the corresponding helix grooves.

22. A safety syringe having a retractable needle facility incorporated therein, the syringe comprising a barrel and plunger and needle assembly, wherein the needle is caused to retract into the barrel of the syringe upon completion of injection once it has been used, by means of engagement between the needle assembly and the end of the plunger, and wherein locking means is provided in the body of the syringe to engage the plunger once it is retracted after use, so that the syringe is rendered incapable of being used further, the locking means provided by a split bush located in the end of the syringe barrel from which the plunger extends and in which the bush is fitted after the plunger is inserted in the barrel and pressed into position in the barrel, wherein the split is made to fit around the shaft of the plunger and is made to reduce in diameter when so pressed into the barrel, and engages by snap fit in the internal region of the barrel and the locking means is provided by a twist lock feature including a twist lock bush having helix grooves therein located in the barrel of the syringe and lugs located on the plunger for engagement in the helix grooves, so that after an injection the plunger is withdrawn and locked in position by twisting the plunger to cause the lugs to move through the corresponding helix grooves and pass completely though the bush.

* * * * *